United States Patent [19]
Stüber et al.

[11] Patent Number: 5,859,185
[45] Date of Patent: Jan. 12, 1999

[54] HCMV-SPECIFIC PEPTIDES, AGENTS THEREFOR AND THE USE THEREOF

[75] Inventors: Werner Stüber, Lahntal; Leszek Wieczorek; Robert Ziegelmaier, both of Marburg, all of Germany

[73] Assignee: Behringwerke Aktiengesellschaft, Marburg, Germany

[21] Appl. No.: 388,883

[22] Filed: Feb. 13, 1995

Related U.S. Application Data

[63] Continuation of Ser. No. 200,305, Feb. 23, 1994, abandoned, which is a continuation of Ser. No. 936,219, Aug. 27, 1992.

[30] Foreign Application Priority Data

Aug. 29, 1991 [DE] Germany .................. P4128684.7

[51] Int. Cl.⁶ .................. C07K 4/02; C07K 14/045; C07K 7/08
[52] U.S. Cl. .................. 530/324; 530/326; 530/327; 530/328; 530/345
[58] Field of Search .................. 435/5, 7.1, 7.92; 530/324, 325, 326, 327, 328, 330, 350, 333, 329, 345

[56] References Cited

FOREIGN PATENT DOCUMENTS

| | | |
|---|---|---|
| 0 252 531 A1 | 1/1988 | European Pat. Off. |
| 0 268 014 A2 | 5/1988 | European Pat. Off. |
| 0 271 201 A2 | 6/1988 | European Pat. Off. |
| WO 89/01628 | 2/1989 | WIPO |

OTHER PUBLICATIONS

Synthesis and Application of Acid Labile Anchor Groups for the Synthesis of Peptide Amides by Fmoc–solid–phase Peptide Synthesis, Breipohl et al., Int. J. Peptide Protein Res., 34: 262–267 (1989).

Mapping of Serologically Relevant Regions of Human Cytomegalovirus Phospho–protein p. 150 Using Synthetic Peptides, Novák et al., Journal of General Virology, 72: 1409–1413 (1991).

Map Position and Nucleotide Sequence of the Gene for the Large Structural Phosphoprotein of Human Cytomegalovirus, G. Jahn. et al., Journal of Virology, 61 (5): 1358–1367 (1987).

Hybridoma Technology in the Biosciences and Medicine, T.A. Springer, ed., Plenum Press NY, London, pp. 355–367 (1985).

Peroxidase–Labeled Antibody, A New Method of Conjugation, Nakane et al., J. of Histochem. and Cytochem., 22 (12): 1084–1091 (1974).

Enzyme–Labeling of Antibodies, Ishikawa et al., Journal of Immunoassay, 4 (3): 209–327 (1983).

Derwent Abstract for EP–A 0 268 014 A2.

*Primary Examiner*—David Guzo
*Attorney, Agent, or Firm*—Finnegan, Henderson, Farabow, Garrett & Dunner, L.L.P.

[57] ABSTRACT

The invention relates to peptides for the immunochemical determination of human cytomegalovirus (HCMV)-specific antibodies and HCMV antigens, and to agents suitable for this method and to the use thereof.

62 Claims, No Drawings

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 40 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 1
        ( D ) OTHER INFORMATION: /note= "Some or all amino acids in
        the regions spanning 0-14 may be absent"

( i x ) FEATURE:
        ( A ) NAME/KEY: Region
        ( B ) LOCATION: 22
        ( D ) OTHER INFORMATION: /note= "Some or all amino acids in
        the regions 22-40 may be absent."

( x i ) SEQUENCE DESCRIPTION: SEQ ID NO:1:

```
Gln  Pro  Thr  Leu  Thr  Phe  Gly  Ala  Gly  Val  Asn  Val  Pro  Ala  Gly  Ala
 1                  5                         10                         15

Gly  Ala  Ala  Ile  Leu  Thr  Pro  Thr  Pro  Val  Asn  Pro  Ser  Thr  Ala  Pro
              20                        25                        30

Ala  Pro  Ala  Pro  Thr  Pro  Thr  Phe
```

```
                      3 5                              4 0
```

(2) INFORMATION FOR SEQ ID NO:2:

(i) SEQUENCE CHARACTERISTICS:
        (A) LENGTH: 41 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Region
        (B) LOCATION: 1
        (D) OTHER INFORMATION: /note= "Some or all amino acids in the regions spanning 0-18 may be absent."

(i x) FEATURE:
        (A) NAME/KEY: Region
        (B) LOCATION: 24
        (D) OTHER INFORMATION: /note= "Some or all amino acids in the regions spanning 24-41 may be absent."

(x i) SEQUENCE DESCRIPTION: SEQ ID NO:2:

```
Ala  Pro  Thr  Ala  Pro  Leu  Pro  Gly  Asp  Met  Asn  Pro  Ala  Asn  Trp  Pro
 1                  5                        1 0                         1 5

Arg  Glu  Arg  Ala  Trp  Ala  Leu  Lys  Asn  Pro  His  Leu  Ala  Tyr  Asn  Pro
               2 0                      2 5                        3 0

Phe  Arg  Met  Pro  Thr  Thr  Ser  Thr  Ala
          3 5                 4 0
```

(2) INFORMATION FOR SEQ ID NO:3:

(i) SEQUENCE CHARACTERISTICS:
        (A) LENGTH: 28 amino acids
        (B) TYPE: amino acid
        (C) STRANDEDNESS: single
        (D) TOPOLOGY: linear (i i) MOLECULE TYPE: peptide (i x) FEATURE:
        (A) NAME/KEY: Region
        (B) LOCATION: 1
        (D) OTHER INFORMATION: /note= "Some or all amino acids in the regions spanning 0-11 may be absent."

(i x) FEATURE:
        (A) NAME/KEY: Region
        (B) LOCATION: 18
        (D) OTHER INFORMATION: /note= "Some or all amino acids in the regions spanning 18-28 may be absent."

(x i) SEQUENCE DESCRIPTION: SEQ ID NO:3:

```
Pro  Ser  Thr  Pro  Arg  Ala  Ala  Val  Thr  Gln  Thr  Ala  Ser  Arg  Asp  Ala
 1                  5                        1 0                         1 5

Ala  Asp  Glu  Val  Trp  Ala  Leu  Arg  Asp  Gln  Thr  Ala
               2 0                      2 5
```

(2) INFORMATION FOR SEQ ID NO:4:

(i) SEQUENCE CHARACTERISTICS:
        (A) LENGTH: 26 amino acids
        (B) TYPE: amino acid
        (D) TOPOLOGY: linear (i i) MOLECULE TYPE: peptide (x i) SEQUENCE DESCRIPTION: SEQ ID NO:4:

```
Ala  Tyr  Lys  Phe  Glu  Gln  Pro  Thr  Leu  Thr  Phe  Gly  Ala  Gly  Val  Asn
```

```
            1                   5                       10                      15
        Val Pro Ala Gly Ala Gly Ala Ala Ile Leu
                        20                      25
```

(2) INFORMATION FOR SEQ ID NO:5:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:5:

```
        Phe Glu Gln Pro Thr Leu Thr Phe Gly Ala Gly Val Asn Val Pro Ala
        1                   5                       10                      15
        Gly Ala Gly Ala Ala Ile Leu Thr Pro Thr Pro Val
                        20                      25
```

(2) INFORMATION FOR SEQ ID NO:6:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:6:

```
        Phe Glu Gln Pro Thr Leu Thr Phe Gly Ala Gly Val Asn Val Pro Ala
        1                   5                       10                      15
        Gly Ala Gly Ala Ala Ile Leu Thr Pro Thr Pro Val Asn Pro Ser Thr
                        20                      25                      30
        Ala
```

(2) INFORMATION FOR SEQ ID NO:7:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:7:

```
        Gln Pro Thr Leu Thr Phe Gly Ala Gly Val Asn Val Pro Ala Gly Ala
        1                   5                       10                      15
        Gly Ala Ala Ile Leu Thr Pro Thr Pro Val Asn Pro Ser Thr Ala Pro
                        20                      25                      30
        Ala Pro Ala
                35
```

(2) INFORMATION FOR SEQ ID NO:8:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (xi) SEQUENCE DESCRIPTION: SEQ ID NO:8:

```
        Pro Thr Leu Thr Phe Gly Ala Gly Val Asn Val Pro Ala Gly Ala Gly
        1                   5                       10                      15
        Ala Ala Ile Leu Thr Pro Thr Pro Val Asn Pro Ser Thr Ala Pro Ala
```

20                        25                         30

Pro  Ala ( 2 ) INFORMATION FOR SEQ ID NO:9:

( i ) SEQUENCE CHARACTERISTICS:
                ( A ) LENGTH: 35 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:9:

Pro  Thr  Leu  Thr  Phe  Gly  Ala  Gly  Val  Asn  Val  Pro  Ala  Gly  Ala  Gly
          1                   5                        10                        15

Ala  Ala  Ile  Leu  Thr  Pro  Thr  Pro  Val  Asn  Pro  Ser  Thr  Ala  Pro  Ala
                              20                        25                        30

Pro  Ala  Pro
                    35

( 2 ) INFORMATION FOR SEQ ID NO:10:

( i ) SEQUENCE CHARACTERISTICS:
                ( A ) LENGTH: 19 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:10:

Val  Asn  Val  Pro  Ala  Gly  Ala  Gly  Ala  Ala  Ile  Leu  Thr  Pro  Thr  Pro
          1                   5                        10                        15

Val  Asn  Pro ( 2 ) INFORMATION FOR SEQ ID NO:11:

( i ) SEQUENCE CHARACTERISTICS:
                ( A ) LENGTH: 21 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:11:

Pro  Ala  Gly  Ala  Gly  Ala  Ala  Ile  Leu  Thr  Pro  Thr  Pro  Val  Asn  Pro
          1                   5                        10                        15

Ser  Thr  Ala  Pro  Ala
                              20

( 2 ) INFORMATION FOR SEQ ID NO:12:

( i ) SEQUENCE CHARACTERISTICS:
                ( A ) LENGTH: 31 amino acids
                ( B ) TYPE: amino acid
                ( D ) TOPOLOGY: linear ( i i ) MOLECULE TYPE: peptide ( x i ) SEQUENCE DESCRIPTION: SEQ ID NO:12:

Val  Asn  Val  Pro  Ala  Gly  Ala  Gly  Ala  Ala  Ile  Leu  Thr  Pro  Thr  Pro
          1                   5                        10                        15

Val  Asn  Pro  Ser  Thr  Ala  Pro  Ala  Pro  Ala  Pro  Thr  Pro  Thr  Phe
                              20                        25                        30

( 2 ) INFORMATION FOR SEQ ID NO:13:

(i) SEQUENCE CHARACTERISTICS:
    (A) LENGTH: 31 amino acids
    (B) TYPE: amino acid
    (D) TOPOLOGY: linear (ii) MOLECULE TYPE: peptide (xi) SEQUENCE DESCRIPTION: SEQ ID NO:13:

```
Pro Ala Gly Ala Gly Ala Ala Ile Leu Thr Pro Thr Pro Val Asn Pro
 1               5                  10                      15
Ser Thr Ala Pro Ala Pro Ala Pro Thr Pro Thr Phe Ala Gly Thr
            20                  25                  30
```

(2) INFORMATION FOR SEQ ID NO:14:

(i) SEQUENCE CHARACTERISTICS:
    (A) LENGTH: 30 amino acids
    (B) TYPE: amino acid
    (D) TOPOLOGY: linear (ii) MOLECULE TYPE: peptide (xi) SEQUENCE DESCRIPTION: SEQ ID NO:14:

```
Gly Ala Gly Val Asn Val Pro Ala Gly Ala Gly Ala Ala Ile Leu Thr
 1               5                  10                      15
Pro Thr Pro Val Asn Pro Ser Thr Ala Pro Ala Pro Ala Pro
            20                  25                  30
```

(2) INFORMATION FOR SEQ ID NO:15:

(i) SEQUENCE CHARACTERISTICS:
    (A) LENGTH: 32 amino acids
    (B) TYPE: amino acid
    (D) TOPOLOGY: linear (ii) MOLECULE TYPE: peptide (xi) SEQUENCE DESCRIPTION: SEQ ID NO:15:

```
Gly Ala Gly Ala Ala Ile Leu Thr Pro Thr Pro Val Asn Pro Ser Thr
 1               5                  10                      15
Ala Pro Ala Pro Ala Pro Thr Pro Thr Phe Ala Gly Thr Gln Thr Pro
            20                  25                  30
```

(2) INFORMATION FOR SEQ ID NO:16:

(i) SEQUENCE CHARACTERISTICS:
    (A) LENGTH: 36 amino acids
    (B) TYPE: amino acid
    (D) TOPOLOGY: linear (ii) MOLECULE TYPE: peptide (xi) SEQUENCE DESCRIPTION: SEQ ID NO:16:

```
Gln Pro Thr Leu Thr Phe Gly Ala Gly Val Asn Val Pro Ala Gly Ala
 1               5                  10                      15
Gly Ala Ala Ile Leu Thr Pro Thr Pro Val Asn Pro Ser Thr Ala Pro
            20                  25                  30
Ala Pro Ala Pro
        35
```

(2) INFORMATION FOR SEQ ID NO:17:

(i) SEQUENCE CHARACTERISTICS:
    (A) LENGTH: 51 amino acids
    (B) TYPE: amino acid
    (D) TOPOLOGY: linear (i i) MOLECULE TYPE: peptide (x i) SEQUENCE DESCRIPTION: SEQ ID NO:17:

| Ala | Tyr | Lys | Phe | Glu | Gln | Pro | Thr | Leu | Thr | Phe | Gly | Ala | Gly | Val | Asn |
| 1 | | | | 5 | | | | | 10 | | | | | | 15 |

| Val | Pro | Ala | Gly | Ala | Gly | Ala | Ala | Ile | Leu | Thr | Pro | Thr | Pro | Val | Asn |
| | | | | 20 | | | | | 25 | | | | | 30 | |

| Pro | Ser | Thr | Ala | Pro | Ala | Pro | Ala | Pro | Thr | Pro | Thr | Phe | Ala | Gly | Thr |
| | | | 35 | | | | | 40 | | | | | 45 | | |

| Gln | Thr | Pro |
| | | 50 |

(2) INFORMATION FOR SEQ ID NO:18:

(i) SEQUENCE CHARACTERISTICS:
      (A) LENGTH: 41 amino acids
      (B) TYPE: amino acid
      (D) TOPOLOGY: linear (i i) MOLECULE TYPE: peptide (x i) SEQUENCE DESCRIPTION: SEQ ID NO:18:

| Ala | Tyr | Lys | Phe | Glu | Gln | Pro | Thr | Leu | Thr | Phe | Gly | Ala | Gly | Val | Asn |
| 1 | | | | 5 | | | | | 10 | | | | | | 15 |

| Val | Pro | Ala | Gly | Ala | Gly | Ala | Ala | Ile | Leu | Thr | Pro | Thr | Pro | Val | Asn |
| | | | | 20 | | | | | 25 | | | | | 30 | |

| Pro | Ser | Thr | Ala | Pro | Ala | Pro | Ala | Pro |
| | | | 35 | | | | | 40 |

(2) INFORMATION FOR SEQ ID NO:19:

(i) SEQUENCE CHARACTERISTICS:
      (A) LENGTH: 29 amino acids
      (B) TYPE: amino acid
      (D) TOPOLOGY: linear (i i) MOLECULE TYPE: peptide (x i) SEQUENCE DESCRIPTION: SEQ ID NO:19:

| Gly | Ala | Gly | Val | Asn | Val | Pro | Ala | Gly | Ala | Gly | Ala | Ala | Ile | Leu | Thr |
| 1 | | | | 5 | | | | | 10 | | | | | | 15 |

| Pro | Thr | Pro | Val | Asn | Pro | Ser | Thr | Ala | Pro | Ala | Pro | Ala |
| | | | | 20 | | | | | 25 | | | |

(2) INFORMATION FOR SEQ ID NO:20:

(i) SEQUENCE CHARACTERISTICS:
      (A) LENGTH: 25 amino acids
      (B) TYPE: amino acid
      (D) TOPOLOGY: linear (i i) MOLECULE TYPE: peptide (x i) SEQUENCE DESCRIPTION: SEQ ID NO:20:

| Asp | Met | Asn | Pro | Ala | Asn | Trp | Pro | Arg | Glu | Arg | Ala | Trp | Ala | Leu | Lys |
| 1 | | | | 5 | | | | | 10 | | | | | | 15 |

| Asn | Pro | His | Leu | Ala | Tyr | Asn | Pro | Phe |
| | | | 20 | | | | | 25 |

(2) INFORMATION FOR SEQ ID NO:21:

(i) SEQUENCE CHARACTERISTICS:
      (A) LENGTH: 20 amino acids
      (B) TYPE: amino acid (D) TOPOLOGY: linear (ii) MOLECULE TYPE: peptide (xi) SEQUENCE DESCRIPTION: SEQ ID NO:21:

Asp Met Asn Pro Ala Asn Trp Pro Arg Glu Arg Ala Trp Ala Leu Lys
1               5                   10                  15
Asn Pro His Leu
            20

(2) INFORMATION FOR SEQ ID NO:22:

(i) SEQUENCE CHARACTERISTICS:
    (A) LENGTH: 17 amino acids
    (B) TYPE: amino acid
    (D) TOPOLOGY: linear (ii) MOLECULE TYPE: peptide (xi) SEQUENCE DESCRIPTION: SEQ ID NO:22:

Pro Ala Asn Trp Pro Arg Glu Arg Ala Trp Ala Leu Lys Asn Pro His
1               5                   10                  15
Leu (2) INFORMATION FOR SEQ ID NO:23:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO:23:

Pro Ala Asn Trp Pro Arg Glu Arg Ala Trp Ala Leu Lys Asn Pro His
1               5                   10                  15
Leu Ala Tyr Asn
            20

(2) INFORMATION FOR SEQ ID NO:24:

(i) SEQUENCE CHARACTERISTICS:
    (A) LENGTH: 20 amino acids
    (B) TYPE: amino acid
    (D) TOPOLOGY: linear (ii) MOLECULE TYPE: peptide (xi) SEQUENCE DESCRIPTION: SEQ ID NO:24:

Trp Pro Arg Glu Arg Ala Trp Ala Leu Lys Asn Pro His Leu Ala Tyr
1               5                   10                  15
Asn Pro Phe Arg
            20

(2) INFORMATION FOR SEQ ID NO:25:

(i) SEQUENCE CHARACTERISTICS:
    (A) LENGTH: 21 amino acids
    (B) TYPE: amino acid
    (D) TOPOLOGY: linear (ii) MOLECULE TYPE: peptide (xi) SEQUENCE DESCRIPTION: SEQ ID NO:25:

Glu Arg Ala Trp Ala Leu Lys Asn Pro His Leu Ala Tyr Asn Pro Phe
1               5                   10                  15

```
            Arg  Met  Pro  Thr  Thr
                            2 0
```

( 2 ) INFORMATION FOR SEQ ID NO:26:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:26:

```
Asp  Met  Asn  Pro  Ala  Asn  Trp  Pro  Arg  Glu  Arg  Ala  Trp  Ala  Leu
 1                  5                        1 0                      1 5
```

( 2 ) INFORMATION FOR SEQ ID NO:27:

( i ) SEQUENCE CHARACTERISTICS:
  ( A ) LENGTH: 17 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:27:

```
Ala  Asn  Trp  Pro  Arg  Glu  Arg  Ala  Trp  Ala  Leu  Lys  Asn  Pro  His  Leu
 1                  5                        1 0                      1 5
Ala
```

( 2 ) INFORMATION FOR SEQ ID NO:28:

( i ) SEQUENCE CHARACTERISTICS:
  ( A ) LENGTH: 33 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:28:

```
Asp  Met  Asn  Pro  Ala  Asn  Trp  Pro  Arg  Glu  Arg  Ala  Trp  Ala  Leu  Lys
 1                  5                        1 0                      1 5
Asn  Pro  His  Leu  Ala  Tyr  Asn  Pro  Phe  Arg  Met  Pro  Thr  Thr  Ser  Thr
                2 0                  2 5                      3 0
Ala
```

( 2 ) INFORMATION FOR SEQ ID NO:29:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:29:

```
Arg  Ala  Trp  Ala  Leu  Lys  Asn  Pro  His  Leu  Ala  Tyr  Asn  Pro  Phe
 1                  5                        1 0                      1 5
```

( 2 ) INFORMATION FOR SEQ ID NO:30:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:30:

Pro Arg Ala Ala Val Thr Gln Thr Ala Ser Arg Asp Ala Ala
1               5                       10

( 2 ) INFORMATION FOR SEQ ID NO:31:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

Ala Ser Arg Asp Ala Ala Asp Glu Val Trp Ala Leu Arg Asp Gln Thr
1               5                       10                      15

Ala ( 2 ) INFORMATION FOR SEQ ID NO:32:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Phe Ala Phe Ala Phe
1               5

( 2 ) INFORMATION FOR SEQ ID NO:33:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

Asp Pro Arg Phe Thr Asp Thr Leu Val Asp Ile Thr Asp Thr Glu Thr
1               5                       10                      15

Ser Ala Lys Pro Pro Val Thr Thr Ala Tyr Lys Phe Glu Gln Pro Thr
                20                      25                      30

Leu Thr Phe Gly Ala Gly Val Asn Val Pro Ala Gly Ala Gly Ala Ala
                35                      40                      45

Ile Leu Thr Pro Thr Pro Val Asn Pro Ser Thr Ala Pro Ala Pro Ala
            50                      55                      60

Pro Thr Pro Thr Phe Ala Gly Thr Gln Thr Pro Val Asn Gly Asn Ser
65                      70                      75                      80

Pro Trp Ala Pro Thr Ala Pro Leu Pro Gly Asp Met Asn Pro Ala Asn
                        85                      90                      95

Trp Pro Arg Glu Arg Ala Trp Ala Leu Lys Asn Pro His Leu Ala Tyr
                100                     105                     110

Asn Pro Phe Arg Met Pro Thr Thr Ser Thr Ala Ser Gln Asn Thr Val
                115                     120                     125

Ser Thr Thr Pro Arg Arg Pro Ser Thr Pro Arg Ala Ala Val Thr Gln
            130                     135                     140

Thr Ala Ser Arg Asp Ala Ala Asp Glu Val Trp Ala Leu Arg Asp Gln
145                     150                     155                     160

Thr Ala ( 2 ) INFORMATION FOR SEQ ID NO:34:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
Asp  Pro  Arg  Phe  Thr  Asp  Thr  Leu  Val  Asp  Ile  Thr  Asp  Thr  Glu  Thr
 1                  5                        10                       15
Ser  Ala  Lys  Pro  Pro  Val
                20
```

( 2 ) INFORMATION FOR SEQ ID NO:35:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

```
Ala  Pro  Ala  Pro  Ala  Pro  Thr  Pro  Thr  Phe  Ala  Gly  Thr  Gln  Thr  Pro
 1                  5                        10                       15
Val  Asn  Gly  Asn  Ser
                20
```

( 2 ) INFORMATION FOR SEQ ID NO:36:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

```
Ala  Pro  Thr  Ala  Pro  Leu  Pro  Gly  Asp  Met  Asn  Pro  Ala
 1                  5                        10
```

( 2 ) INFORMATION FOR SEQ ID NO:37:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:37:

```
Gln  Asn  Thr  Val  Ser  Thr  Thr  Pro  Arg  Arg  Pro  Ser  Thr  Pro  Arg  Ala
 1                  5                        10                       15
Ala  Val  Thr  Gln  Thr  Ala
                20
```

( 2 ) INFORMATION FOR SEQ ID NO:38:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:38:

Gly Thr Gln Thr Pro Val Asn Gly Asn Ser Pro Trp Ala Pro Thr Ala
1               5                   10                  15

( 2 ) INFORMATION FOR SEQ ID NO:39:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:39:

Pro Val Thr Thr Ala Tyr Lys Phe Glu Gln Pro Thr Leu Thr Phe
1               5                   10                  15

( 2 ) INFORMATION FOR SEQ ID NO:40:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:40:

Leu Thr Phe Gly Ala Gly Val Asn Val Pro Ala Gly Ala Gly Ala Ala
1               5                   10                  15

Ile Leu ( 2 ) INFORMATION FOR SEQ ID NO:41:

( i ) SEQUENCE CHARACTERISTICS:
      ( A ) LENGTH: 14 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:41:

Ile Leu Thr Pro Thr Pro Val Asn Pro Ser Thr Ala Pro Ala
1               5                   10

( 2 ) INFORMATION FOR SEQ ID NO:42:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:42:

Pro Phe Arg Met Pro Thr Thr Ser Thr Ala Ser Gln Asn Thr Val
1               5                   10                  15

( 2 ) INFORMATION FOR SEQ ID NO:43:

( i ) SEQUENCE CHARACTERISTICS:
      ( A ) LENGTH: 15 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:43:

Glu Thr Ser Ala Lys Pro Pro Val Thr Thr Ala Tyr Lys Phe Glu (2) INFORMATION FOR SEQ ID NO:44:

(i) SEQUENCE CHARACTERISTICS:
    (A) LENGTH: 13 amino acids
    (B) TYPE: amino acid
    (D) TOPOLOGY: linear (ii) MOLECULE TYPE: peptide (xi) SEQUENCE DESCRIPTION: SEQ ID NO:44:

Lys Phe Glu Gln Pro Thr Leu Thr Phe Gly Ala Gly Val
   1               5                  10

(2) INFORMATION FOR SEQ ID NO:45:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:45:

Ala Gly Ala Ala Ile Leu Thr Pro Thr Pro Val
   1               5                  10

(2) INFORMATION FOR SEQ ID NO:46:

(i) SEQUENCE CHARACTERISTICS:
    (A) LENGTH: 12 amino acids
    (B) TYPE: amino acid
    (D) TOPOLOGY: linear (ii) MOLECULE TYPE: peptide (xi) SEQUENCE DESCRIPTION: SEQ ID NO:46:

Val Asn Pro Ser Thr Ala Pro Ala Pro Ala Pro Thr
   1               5                  10

(2) INFORMATION FOR SEQ ID NO:47:

(i) SEQUENCE CHARACTERISTICS:
    (A) LENGTH: 15 amino acids
    (B) TYPE: amino acid
    (D) TOPOLOGY: linear (ii) MOLECULE TYPE: peptide (xi) SEQUENCE DESCRIPTION: SEQ ID NO:47:

His Leu Ala Tyr Asn Pro Phe Arg Met Pro Thr Thr Ser Thr Ala
   1               5                  10                  15

(2) INFORMATION FOR SEQ ID NO:48:

(i) SEQUENCE CHARACTERISTICS:
    (A) LENGTH: 11 amino acids
    (B) TYPE: amino acid
    (D) TOPOLOGY: linear (ii) MOLECULE TYPE: peptide (xi) SEQUENCE DESCRIPTION: SEQ ID NO:48:

Asp Pro Arg Phe Thr Asp Thr Leu Val Asp Ile
   1               5                  10

(2) INFORMATION FOR SEQ ID NO:49:

-continued (i) SEQUENCE CHARACTERISTICS:
    (A) LENGTH: 23 amino acids
    (B) TYPE: amino acid
    (D) TOPOLOGY: linear (ii) MOLECULE TYPE: peptide (xi) SEQUENCE DESCRIPTION: SEQ ID NO:49:

```
Ile Thr Asp Thr Glu Thr Ser Ala Lys Pro Pro Val Thr Thr Ala Tyr
 1               5                  10                      15
Lys Phe Glu Gln Pro Thr Leu
             20
```

HCMV-SPECIFIC PEPTIDES, AGENTS THEREFOR AND THE USE THEREOF

This application is a continuation of application Ser. No. 08/200,305, filed Feb. 23, 1994, now abandoned, which is a continuation of application Ser. No. 07/936,219, filed Aug. 27, 1992, abandoned.

The invention relates to peptides for the immunochemical determination of human cytomegalovirus (HCMV)-specific antibodies and HCMV antigens, and to agents suitable for this method and to the use thereof.

Used to date in diagnosis to check the HCMV immunity status has been, for example, an enzyme immunoassay. This assay detected antibodies specifically directed against HCMV. The antigen employed was virus material which was generally grown on human fibroblasts in an elaborate cell culture and, after processing, attached to a surface utilizable in diagnosis, for example an ELISA microtiter plate.

Obtaining HCMV antigen for antibody detection from cell culture is generally very time-consuming and costly and is associated with a possible risk of infection for the people engaged therein. To use this antigen in an immuno-logical diagnostic assay, the virus must be obtained from the cell culture medium or even from the cells themselves or at least be presented in a form which makes an immuno-logical reaction possible. Since further purification of this material by biochemical methods is very elaborate and involves large losses, for example cell-bound virus material is only liberated by ultrasonification and is employed directly after dilution for coating microtiter plates, for example. In this case it is not only virus-specific structures which are bound to the surfaces of the microtiter plate wells but also to a greater extent cell-specific proteins. The latter in turn may with certain diseases, for example autoimmune diseases, easily lead to false-positive results and accordingly to misdiagnosis. To determine the number of false-positive signals, generally investigation material from non-infected cell cultures is therefore used as control. This inevitably doubles the complexity of the assay and the costs per sample. A distinct improvement in the described method is represented by the use of recombinant proteins which can be prepared in high yield in a heterologous system, for example in *Escherichia coli*. Possible HCMV infection is generally ruled out by cloning and expression of defined regions of the virus. In addition there is a possibility of a differential diagnosis directed at specific virus proteins. However, to employ recombinant proteins in immunological assays it must be ensured that no contaminating constituents of the host cell lead to false-positive reactions with serum samples. Specific, usually very elaborate purification methods are needed in this case to achieve this quality.

Furthermore, the recombinant proteins must carry immunologically reactive epitopes which unambiguously define the immune status and have a diagnostic relevance or a relevance for the production of a protective status (vaccine). In most cases these epitopes cannot be prepared in native form by recombinant techniques because they represent foreign proteins for most of the expression systems used and rapidly undergo proteolytic degradation. For this reason they are usually expressed as hybrid proteins, with a host-protein for example β-galactosidase in the case of *Escherichia coli*, as fusion partner stabilizing the expression product. However, this foreign portion of the fusion may, owing to the following purification steps, give rise to false-positive reactions which impede the diagnostic use of recombinant proteins.

A protein has now been identified which is generally suitable for determining the immune status for HCMV. For this protein, the protein pp150, both the complete DNA sequence as well as a section 162 amino acids long (the XhoI-PstI restriction fragment, called pXP1 cloned as plasmid) are known which contains sequences relevant for unambiguous diagnosis (Jahn, G. et al. (1987), J. Virol. 61, 1358-1367).

J. Novak et al. (J. Novak et al. (1991), J. Gen. Virol. 72, 1409–1413) have now found, with the aid of synthetically prepared peptides, on the complete pp150 protein only three immunoreactive regions, of which two regions are located between the cleavage sites of the restriction endonucleases XhoI and PstI (XP1 region, Tab. 1).

The amino acids are reproduced in Tab. 1 as single letter code according to the following key: Ala=A, Arg=R, Asn=N, Asp=D, Cys=C, Gln=Q, Glu=E, Gly=G, His=H, Ile=I, Leu=L, Lys=K, Met=M, Phe=F, Pro=P, Ser=S, Thr=T, Trp=W, Tyr=Y and Val=V.

The object on which the present invention was based was first to develop an assay with which it is possible to detect HCMV infections as early as possible and with high specificity.

Surprisingly, it has now been found, that it was not possible to confirm the immunoreactive regions found by Novak et al. on the XP1 region but, instead of this, three immunoreactive regions different from Novak et al. were found. It was additionally found that virtually complete determination of the immune status is possible in particular by using all three epitopes according to the invention in an immunoassay.

The invention therefore relates to peptides which react specifically with antibodies against HCMV, and which contain at least one of the following amino-acid sequences:

$AS_e$-gly ala gly ala ala ile leu-$BS_m$ (peptide 1)(SEQ ID NO:1)

$CS_n$-arg ala trp ala leu -$DS_o$(peptide 2)(SEQ ID NO:2) and/or $ES_p$-ala ser arg asp ala ala-$FS_q$ (peptide 3) (SEQ ID NO:3) where AS, BS, CS, DS, ES and FS are, independently of one another, any appropriate amino acid and

| | |
|---|---|
| e | are, independently of one another, integers from 0 to 22, |
| m | are, independently of one another, integers from 0 to 25, |
| n and o | are, independently of one another, integers from 0 to 18 |
| and | |
| p and q | are, independently of one another, integers from 0 to 11. |

Preferred peptides are
for peptide 1
1.1 (SEQ ID NO:4)
ala tyr lys phe glu gln pro thr leu thr phe gly ala gly val asn val pro ala gly ala gly ala ala ile leu
1.2 (SEQ ID NO:5)
phe glu gln pro thr leu thr phe gly ala gly val asn val pro ala gly ala gly ala ala ile leu thr pro thr pro val
1.3 (SEQ ID NO:6)
phe glu gln pro thr leu thr phe gly ala gly val asn val pro ala gly ala gly ala ala ile leu thr pro thr pro val asn pro ser thr ala
1.4 (SEQ ID NO:7)
phe glu gln pro thr leu thr phe gly ala gly val asn val pro ala gly ala gly ala ala ile leu thr pro thr pro val asn pro ser thr ala pro ala pro ala 1.5 (SEQ ID NO:8)

pro thr leu thr phe gly ala gly val asn val pro ala gly ala gly ala ala ile leu thr pro thr pro val asn pro ser thr ala pro ala pro ala 1.6 (SEQ ID NO:9)

pro thr leu thr phe gly ala gly val asn val pro ala gly ala gly ala ala ile leu thr pro thr pro val asn pro ser thr ala pro ala pro ala pro NH$_2$ 1.7 (SEQ ID NO:10)

val asn val pro ala gly ala gly ala ala ile leu thr pro thr pro val asn pro 1.8 (SEQ ID NO:11)

pro ala gly ala gly ala ala ile leu thr pro thr pro val asn pro ser thr ala pro ala 1.9 (SEQ ID NO:12)

val asn val pro ala gly ala gly ala ala ile leu thr pro thr pro val asn pro ser thr ala pro ala pro ala pro thr pro thr phe 1.10 (SEQ ID NO: 13)

pro ala gly ala gly ala ala ile leu thr pro thr pro val asn pro ser thr ala pro ala pro ala pro thr pro thr phe ala gly thr 1.11 (SEQ ID NO:14)

gly ala gly val asn val pro ala gly ala gly ala ala ile leu thr pro thr pro val asn pro ser thr ala pro ala pro ala pro NH$_2$ 1.12 (SEQ ID NO:15)

gly ala gly ala ala ile leu thr pro thr pro val asn pro ser thr ala pro ala pro ala pro thr pro thr phe ala gly thr gln thr pro 1.13 (SEQ ID NO:16)

ala tyr lys phe gly gln pro thr leu thr phe gly ala gly val asn val pro ala gly ala gly ala ala ile leu thr pro thr pro val asn pro ser thr ala pro ala pro ala pro 1.14 (SEQ ID NO:17)

ala tyr lys phe glu gln pro thr leu thr phe gly ala gly val asn val pro ala gly ala gly ala ala ile leu thr pro thr pro val asn pro ser thr ala pro ala pro ala pro thr pro thr phe ala gly thr gln thr pro 1.15 (SEQ ID NO:18)

ala tyr lys phe glu gln pro thr leu thr phe gly ala gly val asn val pro ala gly ala gly ala ala ile leu thr pro thr pro val asn pro ser thr ala pro ala pro ala pro NH$_2$ 1.16 (SEQ ID NO:19)

gly ala gly val asn val pro ala gly ala gly ala ala ile leu thr pro thr pro val asn pro ser thr ala pro ala pro ala for peptide 2

2.1 (SEQ ID NO:20)

asp met asn pro ala asn trp pro arg glu arg ala trp ala leu lys asn pro his leu ala tyr asn pro phe 2.2 (SEQ ID NO:21)

asp met asn pro ala asn trp pro arg glu arg ala trp ala leu lys asn pro his leu 2.3 (SEQ ID NO:22)

pro ala asn trp pro arg glu arg ala trp ala leu lys asn pro his leu 2.4 (SEQ ID NO:23)

pro ala asn trp pro arg glu arg ala trp ala leu lys asn pro his leu ala tyr asn 2.5 (SEQ ID NO:24)

trp pro arg glu arg ala trp ala leu lys asn pro his leu ala tyr asn pro phe arg 2.6 (SEQ ID NO:25)

glu arg ala trp ala leu lys asn pro his leu ala tyr asn pro phe arg met pro thr thr 2.7 (SEQ ID NO:26)

asp met asn pro ala asn trp pro arg glu arg ala trp ala leu 2.8 (SEQ ID NO:27)

ala asn trp pro arg glu arg ala trp ala leu lys asn pro his leu ala 2.9 (SEQ ID NO:28)

asp met asn pro ala asn trp pro arg glu arg ala trp ala leu lys asn pro his leu ala tyr asn pro phe arg met pro thr thr ser thr ala 2.10 (SEQ ID NO:29)

arg ala trp ala leu lys asn pro his leu ala tyr asn pro phe for peptide 3

3.1 (SEQ ID NO:30)

pro arg ala ala val thr gln thr ala ser arg asp ala ala 3.2 (SEQ ID NO:31)

ala ser arg asp ala ala asp glu val trp ala leu arg asp gln thr ala

Of these, the following peptides are particularly preferred:

for peptide 1

1.3, (SEQ ID NO:6) 1.4, (SEQ ID NO:7) 1.6, (SEQ ID NO 9) 1.11, (SEQ ID NO:14) 1.13 (SEQ ID NO:14)

for peptide 2

2.1, (SEQ ID NO:20) 2.5, (SEQ ID NO:24) 2.9 (SEQ ID NO:28) and/or 2.10 (SEQ ID NO:29)

for peptide 3

3.2 (SEQ ID NO:31)

The expressions peptides and polypeptides are used for the purpose of the invention as equivalent to peptides and proteins with up to about 80 AA.

By immunoreactive peptides are generally meant peptides with at least one epitope, where the minimum length of the peptides is generally approximately 6, preferably approximately 8–10 amino acids.

It is often advantageous to derivatize peptides in a variety of ways, such as, for example, by amino-terminal or carboxy-terminal attachment of one or more amino acids, preferably cysteine, in order, for example, to achieve linkage of peptides with one another or to a support. The extensions generally comprise 1 to 40, preferably 1 to 20, in particular 1 to 10 amino acids.

Other examples are thioglycolic acid amidation, carboxy-terminal amidation such as, for example, with ammonia or methylamine. Modifications of these types may alter the net charge on the polypeptide and improve the physicochemical properties of the peptide or facilitate covalent bonding of the peptide to a solid support, to carrier protein or to another peptide.

It is furthermore also possible by replacing individual amino acids by structurally related amino acids to generate immunoreactive mutants. Thus, for example, the amino acid al can be replaced by leu, ile or amino acids which do not occur naturally, such as nva.

In general, modifications of this type do not result in direction alterations in the immunoreactivity of a peptide, although it is perfectly possible to achieve improved immunological properties of the peptides. Thus, for example, methionine is prone to spontaneous oxidation, which can be prevented by replacement by norleucine, without essentially changing the antigenic properties of the polypeptide.

Other amino-acid replacements can take place, for example, within the following groups: gly, ala; val, ile, leu; asp, glu; asn, gln; ser, thr; lys, arg; phe, tyr; ala, ser; ala, thr; ala, val; ala, pro; ala, glu; leu, gln; gly, phe; ile, ser and ile, met.

The invention therefore also relates to peptides with an amino-acid sequence according to the invention modified by replacement, addition or deletion of one or more amino acids.

It may likewise be advantageous to improve the polypeptide's properties of adsorption onto a support by the addition of a hydrophobic sequence comprising about 2 to 20 hydrophobic amino acids such as, for example, phe ala phe (SEQ ID NO:32) ala phe.

It has also been found that mixtures of the peptides according to the invention may have better diagnostic properties than single peptides for an immunochemical anti-HCMV detection.

The invention therefore also relates to mixtures of the peptides according to the invention.

Mixtures of peptides 1, 2 and 3 are particularly suitable, and in turn the following mixtures are particularly preferred: 1.6, (SEQ ID NO:9) 2.1, (SEQ ID NO:20) 3.2; (SEQ ID NO:31) 1.11, (SEQ ID NO:14) 2.1, (SEQ ID NO:20) 3.2; 1.6, 2.10, 3.2; (SEQ ID NO:31) 1.11, 2.10, (SEQ ID NO:29) 3.2; 1.6, (SEQ ID NO:9) 2.7, 3.2 or 1.11, 2.7, 3.2 (SEQ ID NO:31).

However, if a mixture is prepared from the peptides and used to coat, for example, a microtiter plate, there is a risk of unequal coating since the peptides vary in their efficiency of binding to the surface owing to different physical properties.

In another embodiment, therefore, 2 or more of the said peptides, preferably 2 to 10, in particular 2 to 4, peptides are linked with or without spacer. This results in uniform coating of the microtiter plates. It is even possible to prepare polymeric forms of two or more peptides by methods known to the person skilled in the art, so that multiple immunorelevant epitopes are present on one peptide. The peptides according to the invention can, as already mentioned, also be bound to a carrier such as, for example, protein or latex particle. Thus, particularly suitable as carrier or else as bridge are, for example, human serum albumin and/or polylysine.

Modifications of these types generally alter the passive adsorption or property of covalent bonding to the solid phase in a beneficial way, have an advantageous effect on the coupling method or act more strongly as antigen in the generation of polyclonal or monoclonal antibodies directed against the peptides.

The invention therefore also relates to peptides which are linked together with or without bridge, or can also be bound to a carrier.

The said immunoreactive peptides can be prepared by synthesis or genetic manipulation, preferably by synthesis by methods known to the person skilled in the art.

They can be synthesized both in the form of one peptide and in the form of a mixture of a plurality of small peptides with overlapping or non-overlapping amino-acid sequence.

The polypeptides prepared by genetic manipulation also include fusion proteins whose fusion portion has subsequently been eliminated. They also include polypeptides which can be modified where appropriate, for example, by glycosylation, acetylation or phosphorylation.

Solid-phase synthesis, especially the Fmoc method of G. B. Fields and R. L. Noble has preferably been used for the chemical peptide synthesis. Using this method the peptides according to the invention can be prepared, for example, in a semiautomatic or completely automatic peptide synthesizer on polystyrene (1% divinylbenzene) using anchors suitable for Fmoc. A carboxyl or carboxamide functionality, for example, can be used at the C terminus. In the case of a carboxyl group it is possible and preferable to use alkoxybenzyl alcohol as anchor on the resin. Peptide amides can be synthesized, for example, on [(5-carboxylatoethyl-2,4-dimethoxyphenyl) -4'-methoxyphenyl]methylamine resin by the method of Breipohl et al. (G. Breipohl, J. Knolle and W. Stuber, Int. J. Peptide, Protein Res. 34, 1989, 252–267). The initial loadings of the resins were generally in the range 0.2–1.0 mmol, preferably 0.4–0.6 mmol of amino functionalities/gram. The syntheses were carried out by the following general reaction sequence:

1. Resin washed, for example with DMF.
2. Resin treated with a solvent mixture such as, for example, piperidine/DMF.
3. Resin washed, preferably first with DMF/isopropanol and then with DMF.
4. Resin reacted with a 1–6-fold, preferably 2–4-fold, in particular 2.5–3.5-fold, excess of activated amino-acid derivative, for example of a Fmoc-activated amino acid. The amino-acid derivative was activated, for example, with DIC/HOBt or TBTU/DIPEA in DMF.

Reaction steps 3 and 4 repeated.

After the required peptide had been synthesized the peptides were cleaved off the resin, for example by treatment with 90% TFA, 5% ethanedithiol, 5% resorcinol at room temperature. The peptide which has been cleaved off can subsequently be crystallized from ether and purified by general methods such as HPLC, ion exchange chromatography or gel permeation. The composition of the peptides can be checked by amino-acid analysis and/or mass spectrometry, and the purity can be tested, for example, by HPLC.

Bridged peptides were likewise prepared by generally known methods. The following possibilities, inter alia, exist for the bridging:
A) direct amide linkage;
B) bridging via a peptide with 1 to 10, preferably 1 to 5, in particular 1–3, amino acids;
C) thioether or disulfide bridge.

The peptides bridged with an amino acid or a short peptide can be synthesized by the abovementioned method. An example of a suitable short peptide is a triglycine. Joining the two peptides via a so-called spacer, in particular via a hydrophobic spacer, generally has, as already mentioned, a beneficial effect on the interaction of the microtiter plate. A particularly preferred amino acid as bridging element is, for example, epsilon-amino-caproic acid.

Thioether or disulfide bridges are obtained by synthesizing a maleimide functionality at the N terminus of one peptide and introducing a sulfhydryl group, preferably in the form of cysteine, at the C or N terminus of the other peptide, and subsequently linking the two peptides. This linkage can take place both on a solid support and in solution.

An immunochemical detection generally comprises methods which permit the determination of antigens and/or antibodies in body fluids such as serum, plasma, saliva, cerebrospinal fluid or urine as homogeneous (in solution) or heterogeneous (with solid phase) methods. These are also called immunoassays, and examples are enzyme immunoassay (ELISA or EIA), radioimmunoassay (RIA), immunofluorescence assay (IFA), radioimmunoprecipitation assay (RIPA) or agar gel diffusion assay etc.

These numerous, very different methods differ in specific embodiments, in the marker used for detection or measuring principle (for example photometrically, radiometrically, visually or by aggregation, scattered light or precipitation behavior) and in the solid phases. The person skilled in the art is aware that separation of bound and free sample antibodies or antigen is, although widely used, not absolutely necessary such as, for example, in so-called homogeneous assays. Heterogeneous immunoassays are preferred, especially heterogeneous ELISA methods.

The antibody detection in an immunochemical detection method entails contacting the sample with the described peptide sequences during the procedure, in order to form an antigen-antibody complex in a particular step of the relevant method, or to prevent the formation thereof in competitive and inhibition assays by adding suitable labeled reagents.

The invention therefore also relates to an immunochemical method for the detection and/or for the determination of HCMV antibodies using the peptides according to the invention and to an assay kit therefor.

In the direct methods, the antibodies can be contacted with peptides bound to a solid phase or with labeled peptides or with both, it being irrelevant whether the fundamental method is based as 1-, 2- or multistep method on the principle of the second antibody assay or on the immunometric assay design (double-antigen sandwich) either with identical or different peptides (or peptide mixtures) on the solid phase and as liquid reagent for the detection and in conjunction with specific so-called capture antibodies (for example anti-IgM) or affinity reagents (for example protein A).

The peptides can be linked to the solid phase covalently, by adsorption or by means of specific antibodies or similar affinity methods, for example via the biotin/-avidin complex, but adsorption is preferred.

Suitable as support material for the solid phase are plastics such as polystyrene, polyvinyl chloride, polyamide and other synthetic polymers, natural polymers such as cellulose and derivatized natural polymers such as cellulose acetate and nitrocellulose, as well as glass, especially as glass fibers. Polystyrene is preferred as support material.

The supports can be in the form of beads, rods, tubes and microtiter plates or in the form of suspensions such as, for example, latex particles. Sheet-like structures such as paper strips, disks and membranes are likewise suitable. The surface of the supports can be both permeable and impermeable to aqueous solutions.

Preferred supports are beads, tubes, wells, microparticles, paper strips and membranes. Particularly preferred supports are microtiter plates, latex particles, polystyrene beads or magnetically attractable particles.

The peptide concentration for coating the support is generally about 0.01–20 $\mu$g/ml, preferably 0.01–10 $\mu$g/ml, particularly preferably 2–10 $\mu$g/ml.

It is particularly advantageous to use synthetically prepared polypeptides whose high purity and strong antigenicity allows very small amounts to be used, for example 0.01–2.0 $\mu$g/ml, preferably 0.1–0.5 $\mu$g/ml. The binding capacity of the support, in particular when polystyrene is used, is generally not saturated so that it is normally possible to coat with a plurality of different polypeptides, in particular with 2–5, especially with 3–4, different polypeptides, which is a particular advantage.

When the peptides are used as labeled derivatives for the detection, all coupling techniques known to the person skilled in the art are suitable. It is also possible to apply multistage methods such as, for example, preformed peptide-antibody complexes in which the antibody carries the labeling, or high-affinity systems such as, for example, biotin/avidin with labeling of one of these reactants.

Examples of markers which can be used are radioactive isotopes, fluorescent or chemiluminescent dyes. Markers which can also be used are enzymes which, for example, are detected by chromogenic, luminogenic or fluorogenic substrate systems or by subsequent amplifier systems with a second enzyme which is activated by the first.

The markers preferably used are enzymes, especially the alkaline phosphatase and/or horseradish peroxidase or chemiluminogenic compounds such as, for example, acridinium esters.

The labeling is carried out by methods which are described in the prior art for the said markers. In the case of labeling of the antibodies with peroxidase it is possible to use the periodate technique of NAKANE et al., 1974, J. Histochem. Cytochem. 22, 1084–1090, or a method of ISHIKAWA et al., 1983, J. Immunoassay 4, 209–327, in which the partners are linked by a heterobifunctional reagent.

Besides these methods it is possible to use the peptides for sensitizing suitable surfaces such as, for example, latex or erythrocytes in order to measure automatically or visually the physicochemical changes induced by peptide-specific antibodies, such as, for example, precipitations, aggregation or light scattering. It is known that it is also possible to employ the peptides underivatized for the inhibition of these measurement principles as well as the abovementioned methods.

The antigens can be detected using immunodiagnostic methods which make use of polyclonal or monoclonal antibodies which are prepared using the peptides according to the invention or derivatives thereof. The embodiments suitable for the detection method are known to the person skilled in the art and comprise formation in a particular step of antibody-antigen complexes or inhibition of complex formation in competitive methods by adding a labeled antigen.

The invention therefore also relates to an immunochemical method for the detection and/or determination of HCMV antigen using antibodies against the peptides according to the invention, and the assay kit therefor.

Suitable as solid phases, markers or measurement principle for the establishment of an antigen assay are all the possibilities explained for the corresponding antibody determination, with the competitive principle and the double antibody sandwich technique being particularly preferred as immunochemical method. It is immaterial in this connection whether the methods are designed as 1-, 2- or 3-step methods. Thus, multistep methods can be carried out with unlabeled detection antibodies which are determined with the aid of another antibody which is directed against them and is appropriately labeled. It is advantageous for the generation of the antibodies to modify the peptides in such a way that their immunogenic property is improved as is possible, for example, by coupling to natural proteins, such as, for example, to serum proteins such as gamma globulin or serum albumin, to hemocyanins such as KLH = keyhole limpet hemocyanin or toxoids such as diphtheria or tetanus toxoid (B. S. Schaffhausen in Hybridoma Technologie in the Biosciences and Medicine, ed. T. A. Springer, Plenum Press NY, London 1985).

Finally, the present invention can also be applied when using an immunodiagnostic element which contains the solid phase and, in dry form, a part or else all of the reagents required, and in this case too the new peptides are either present on the solid phase or in the detection reagent or in both, and an antibody determination, an antigen detection or combinations with other analytes is carried out.

The peptides according to the invention can be tested by, for example, coating a microtiter plate with the peptides. The coating is generally carried out in a buffer solution, for example in a carbonate, phosphate or trishydroxymethylaminomethane buffer, preferably in a carbonate buffer. After the coating, the plates were incubated with serum samples in a dilution of 1:1 to 1:250, preferably 1:1 to 1:10, in particular 1:1.5 to 1:2.5. Subsequently the antigen-antibody complex was detected by the methods indicated above, for example using a labeled second antibody against the antigen-antibody complex (immunoassay).

The invention also relates to an immunochemical method and a combination kit therefor for the detection and/or for the determination of a plurality of different antibody specificities each against different pathogens, wherein one or more of the HCMV peptides according to the invention and one or more immunoreactive peptides from other pathogens are immobilized on a support, and the antibodies against them are detected by the abovementioned methods, differentially or non-differentially, preferably differentially.

It is possible to employ in the combination assay virus species related to HCMV, such as, for example, the herpes viruses herpes simplex 1 and/or 2 (HSV ½), Epstein-Barr virus (EBV), varicella zoster virus (VZV) or human herpes virus 6 (HHV 6) and/or unrelated virus species such as, for example, the hepatitis viruses HAV, HBV, HCV or else the viruses HIV1 and HIV2. In particular, it is possible to employ mixtures of HCMV peptides and one or more peptides and/or recombinant proteins of other pathogens in the combination assay, in which case the peptides ought not to have any measurable cross-reactivity with one another.

The peptides according to the invention, the immunoreactive parts and mutants thereof are suitable, for example, for HCMV diagnosis and vaccination. The peptides can also be used as coating antigens for various diagnostic assay systems which operate with various surfaces, for example enzyme immunoassay, magnetic and latex particles, test strips, films and papers manufactured in various ways etc.

One advantage of the immunoreactive peptides according to the invention is a high sensitivity and specificity for the detection of HCMV antibodies so that, besides diluted, it is also possible to use undiluted or only slightly diluted samples. Another advantage of the peptides is that, because of their relatively short sequence length, they can be chemically synthesized simply and in high yield. Chemical synthesis has the advantage that the synthetic peptides are free of cell-specific proteins.

The invention furthermore relates to DNA sequences which code for at least one of the peptides according to the invention.

The invention also relates to an analytical method for the detection and/or for the determination of HCMV, wherein a hybridization reaction which uses at least one nucleic acid probe which in its specific part is complementary to at least one of the DNA sequences according to the invention is employed as specific step.

The invention also relates to polyclonal and/or monoclonal antibodies which are directed against one or more of the peptides according to the invention. The antibodies can be obtained by immunization of a suitable donor, for example a rabbit, with the peptides according to the invention by generally known methods.

The invention also relates to vaccines against HCMV which contain at least one of the peptides according to the invention or antibodies against them.

The invention also relates to an immunoassay which contains at least one of the peptides according to the invention, in particular a heterogeneous immunoassay.

LIST OF ABBREVIATIONS

DIC Diisopropylcarbodiimide
DIPEA Diisopropylethylamine
DMF Dimethylformamide
Bop 1-Benzotriazolyloxytris(dimethylamino)phosphonium hexafluorophosphate
Fmoc Fluorenylmethoxycarbonyl
HOBt Hydroxybenzotriazole
TBTU 2-(1H-Benzotriazol-1-yl)-1,1,3,3-tetramethyluronium tetrafluoroborate The following examples are intended to explain the invention in detail without, however, restricting it thereto:

EXAMPLES

1. Preparation of gly ala gly val asn val pro ala gly ala gly ala ala ile leu thr pro thr pro val asn pro ser thr ala pro ala pro ala pro-amide (peptide 1.11) (SEQ ID NO:14)

1.06 g of Fmoc-amide anchor resin were reacted in a completely automatic peptide synthesizer (Advanced ChemTech®, Louisville, Ky., USA) in accordance with the manufacturer's instructions. The amino-acid excess was 3-fold. The reaction time per amino-acid derivative was 30 minutes. 506 mg of Fmoc-proline was employed, together with 213 mg of HOBt and 697 mg of Bop (in place of TBTU), as first amino acid. 3 Mmol of diisopropylethylamine were added as base. The carboxamide functionality was derivatized with trityl. The synthesis was carried out by the following reaction sequence (for 1 g of resin):

1 Resin washed 3 times with 15 ml of DMF each time
2 Resin treated with 15 ml of 20% piperidine/DMF (3 min)
3 Resin treated with 15 ml of 20% piperidine/DMF (10 min)
4 Resin washed 3 times alternately with DMF/isopropanol
5 Resin washed twice with DMF
6 Amino-acid derivative introduced in 3-fold excess and activated either with DIC/HOBt or with TBTU/DIPEA in DMF and shaken with the resin for 30 min
7 Resin washed twice alternately with DMF/isopropanol At the end of the coupling reactions, the peptide resin was washed with methanol and diethyl ether and dried under high vacuum. 2.36 grams of peptide resin were stirred with 27 ml of trifluoroacetic acid-1.5 gram of resorcinol/1.5 ml of ethanedithiol at room temperature for 1.5 hours and crystallized in diethyl ether. The crude peptide was washed with diethyl ether and dried under high vacuum (yield 1090 mg). The peptide was chromatographed on Sephadex G-25 in 0.5% acetic acid, and the peptide fraction was isolated by freeze drying (yield 654 mg). The purity of the substance was tested by HPLC. The correct composition was confirmed by amino-acid analysis. The peptide content was 86%.

2. Testing of the peptides

A microtiter plate with-96 wells was coated with a synthesized peptide. To do this, a solution of 2.5 µg of peptide per ml of carbonate buffer was made up and introduced in 100 µl portions into the wells for the coating. The peptides were adsorbed onto the surfaces at 4° C. overnight and, after removal of the peptide solution, the wells were washed several times with washing buffer (50 mM Tris, pH 7.2, 10 mM EDTA, 0.2% Tween 20). Then individual human serum samples in a 1:2 dilution were introduced and incubated at 37° C. for 1 hour. After another washing step, the conjugate antibody specific for human IgG antibodies or human IgM antibodies and labeled with peroxidase was added and the mixture was incubated at room temperature for 0.5 hour. The reaction was subsequently stopped by adding 0.5M sulfuric acid and extinction of the individual samples was measured at a wavelength of 450/650 nm in a photometer.

3. Localization of relevant epitopes

To test the immunogenicity, peptides of various length from the complete amino-acid sequence region from 718 to 880 of the HCMV protein ppl5O (Tab. 2 and 3) were synthesized as described in Example 1. Subsequently, as in Example 2, the microtiter plates were coated with the synthesized peptides, and the immunological reactivity was assayed. The result of the series of assays was that all the tested HCMV-positive sera reacted in particular with at least one of the three specific sequence regions, whereas the other sequence regions showed only a weak immunological reaction (Tab. 2 and 3). The three immunologically reactive peptides have the following sequences:

AS$_e$-gly ala gly ala ala ile leu-BS$_m$ (peptide 1) (SEQ ID NO:1)

(0.25 μg/well). After development of the plate with said antibody, the reaction with the peptide 2.7, (SEQ ID NO:26) which had previously been identified as an important epitope, was very clearly distinct. It was concluded from the method for selecting the monoclonal antibody that the identified epitope must have a very important structure which is not even destroyed by denaturation of the complete protein. This monoclonal antibody correspondingly reacts both with the synthesized peptide 2.7 (SEQ ID NO:26) and with the recombinant protein XP1 (SEQ ID NO:33 and the ppl150 protein of HCMV.

TAB. 1

(SEQ ID NO.33)
Amino-acid sequence of XP1 (amino acid 718-880 of HCMV protein pp150)

|     |            |            |            |            |            |
| --- | ---------- | ---------- | ---------- | ---------- | ---------- |
| 1   | DPRFTDTLVD | ITDTETSAKP | PVTTAYKFEQ | PTLTFGAGVN | VPAGAGAAIL |
| 51  | TPTPVNPSTA | PAPAPTPTFA | GTQTPVNGNS | PWAPTAPLPG | DMNPANWPRE |
| 101 | RAWALKNPHL | AYNPFRMPTT | STASQNTVST | TPRRPSTPRA | AVTQTASRDA |
| 151 | ADEVWALRDQ | TA         |            |            |            |

CS$_n$-arg ala trp ala leu -DS$_o$ (peptide 2) (SEQ ID NO: 2) and/or

ES$_p$-ala ser arg asp ala ala-FS$_q$ (peptide 3), (SEQ ID NO:3)

where AS, BS, CS, DS, ES and FS are, independently of one another, any appropriate amino acid and

| | |
|---|---|
| e | are, independently of one another, integers from 0 to 22, |
| m | are, independently of one another, integers from 0 to 25, |
| n and o | are, independently of one another, integers from 0 to 18 |
| and | |
| p and q | are, independently of one another, integers from 0 to 11. |

It was possible in this way to differentiate sera which reacted either with all or else only with one or two sequence regions.

Demonstrably HCMV-negative sera did not react with the three peptides.

4. Diagnostic use of the peptides according to the invention

In order to test the immunoreactivity of the peptides found, a mixture of peptides 1.11, (SEQ ID NO:14) 2.10 (SEQ ID NO:29) and 3.2—(SEQ ID NO:31) total concentration 2.5 μg/ml with a mixing ratio of 1:1:1 (by weight) —were introduced as an antigen into microtiter plates as in Example 2, and the assay was carried out as described therein. Used in this case was a defined and previously tested group of sera which had already been assayed in a conventional assay for IgM and IgG reactivity; reference assays: CMV Enzygnost® IgM-POD and CMV Enzygnost® IgG-POD, Behringwerke AG, Marburg. The indicated assay configuration is very suitable for diagnosing the HCMV immune status both for IgM and for IgG antibody detection (Tab. 4 and 5).

Reaction of the monoclonal antibody 87–55/02 with one of the identified peptide epitopes A monoclonal antibody which has an unambiguous immunological reaction with the HCMV protein ppl150 and one with the recombinant protein section pXP1, measured as immunoblot and ELISA reactivity, was investigated on an ELISA microtiter plate which had been coated with various synthesized peptides in Table 3 at the same concentration

TABLE 2

Individual reactivities of the synthetic peptides from the XP1 region of the HCMV protein ppl150

The individual reactivities of the synthetic pXP1 segments with the assayed group of CMV IgG-positive sera are reported in percent.

1. asp pro arg phe thr asp thr leu val asp ile thr asp thr glu thr ser ala lys pro pro val (SEQ ID NO:34)
   Reactivity 20%
2. ala pro ala pro ala pro thr pro thr phe ala gly thr gln thr pro val asn gly asn ser (SEQ ID NO:34)
   Reactivity 20%
3. ala pro thr ala pro leu pro gly asp met asn pro ala (SEQ ID NO:36)
   Reactivity 30%
4. gln asn thr val ser thr thr pro arg arg pro ser thr pro arg ala ala val thr gln thr ala (SEQ ID NO:37)
   Reactivity 40%
5. asp met asn pro ala asn trp pro arg glu arg ala trp ala leu
   Reactivity 60% (Peptide 2.7) (SEQ ID NO:26)
6. arg ala trp ala leu lys asn pro his leu ala tyr asn pro phe
   Reactivity 80% (Peptide 2.10) (SEQ ID NO:29)
7. gly thr gln thr pro val asn gly asn ser pro trp ala pro thr ala (SEQ ID NO:38)
   Reactivity 20%
8. pro val thr thr ala tyr lys phe glu gln pro thr leu thr phe (SEQ ID NO:39)
   Reactivity 10%
9. leu thr phe gly ala gly val asn val pro ala gly ala gly ala ala ile leu (SEQ ID NO:40)
   Reactivity 60%
10. ile leu thr pro thr pro val asn pro ser thr ala pro ala (SEQ ID NO:41)
    Reactivity 40%
11. pro phe arg met pro thr thr ser thr ala ser gln asn thr val (SEQ ID NO:42)
    Reactivity 60%
12. ala ser arg asp ala ala asp glu val trp ala leu arg asp gln thr ala
    Reactivity 80% (Peptide 3.2) (SEQ ID NO:31)
13. gly ala gly val asn val pro ala gly ala gly ala ala ile leu thr pro thr pro val asn pro ser thr ala pro ala pro ala pro NH2

Reactivity 90% (Peptide 1.11) (SEQ ID NO:14)
14. glu thr ser ala lys pro pro val thr thr ala tyr lys phe glu (SEQ ID NO:43)
Reactivity 10%
15. lys phe glu gln pro thr leu thr phe gly ala gly val (SEQ ID NO:44)
Reactivity 20%
16. ala gly ala ala ile leu thr pro thr pro val (SEQ ID NO:45)
Reactivity 40%
17. val asn pro ser thr ala pro ala pro thr (SEQ ID NO:46)
Reactivity 10%
18. his leu ala tyr asn pro phe arg met pro thr thr ser thr ala (SEQ ID NO:47)
Reactivity 60%
19. pro arg ala ala val thr gln thr ala ser arg asp ala ala
Reactivity 60% (Peptide 3.1) (SEQ ID NO:30)
20. asp pro arg phe thr asp thr leu val asp ile (SEQ ID NO:48)
Reactivity 10%
21. ile thr asp thr glu thr ser ala lys pro pro val thr thr ala tyr lys phe glu gln pro thr leu (SEQ ID NO:49)
Reactivity 20%
22. ala asn trp pro arg glu arg ala trp ala leu lys asn pro his leu ala
Reactivity 70% (Peptide 2.8) (SEQ ID NO:27)
23. asp met asn pro ala asn trp pro arg glu arg ala trp ala leu lys asn pro his leu ala tyr asn pro phe
Reactivity 80% (Peptide 2.1) (SEQ ID NO:20)
24. pro thr leu thr phe gly ala gly val asn val pro ala gly ala gly ala ala ile leu thr pro thr pro val asn pro ser thr ala pro ala pro ala pro NH$_2$
Reactivity 90% (Peptide 1.6) (SEQ ID NO:9)
25. ala tyr lys phe glu gln pro thr leu thr phe gly ala gly val asn val pro ala gly ala gly ala ala ile leu thr pro thr pro val asn pro ser thr ala pro ala pro ala pro NH$_2$
Reactivity 85% (Peptide 1.15) (SEQ ID NO:18)

TABLE 3
Individual reactivities of particularly reactive peptides from the XP1 region of the HCMV protein ppl150
The individual reactivities of the synthetic pXPl 5 segments with the assayed group of CMV IgG-positive sera are reported in percent.
Peptide No. 1
1.1 (SEQ ID NO:4) ala tyr lys phe glu gln pro thr leu thr phe gly ala gly val asn val pro ala gly ala gly ala ala ile leu
Reactivity 80%
1.2 (SEQ ID NO:5) phe glu gln pro thr leu thr phe gly ala gly val asn val pro ala gly ala gly ala ala ile leu thr pro thr pro val
Reactivity 80%
1.3 (SEQ ID NO:6) phe glu gln pro thr leu thr phe gly ala gly val asn val pro ala gly ala gly ala ala ile leu thr pro thr pro val asn pro ser thr ala
Reactivity 85%
1.4 (SEQ ID NO:7) phe glu gln pro thr leu thr phe gly ala gly val asn val pro ala gly ala gly ala ala ile leu thr pro thr pro val asn pro ser thr ala pro ala pro ala
Reactivity 90%
1.5 (SEQ ID NO:8) pro thr leu thr phe gly ala gly val asn val pro ala gly ala gly ala ala ile leu thr pro thr pro val asn pro ser thr ala pro ala pro ala
Reactivity 80%
1.6 (SEQ ID NO:9) pro thr leu thr phe gly ala gly val asn val pro ala gly ala gly ala ala ile leu thr pro thr pro val asn pro ser thr ala pro ala pro ala pro NH$_2$
Reactivity 90%
1.7 (SEQ ID NO:10) val asn val pro ala gly ala gly ala ala ile leu thr pro thr pro val asn pro
Reactivity 70%
1.8 (SEQ ID NO:11) pro ala gly ala gly ala ala ile leu thr pro thr pro val asn pro ser thr ala pro ala
Reactivity 70%
1.9 (SEQ ID NO:12) val asn val pro ala gly ala gly ala ala ile leu thr pro thr pro val asn pro ser thr ala pro ala pro ala pro thr pro thr phe
Reactivity 70%
1.10 (SEQ ID NO:13) pro ala gly ala gly ala ala ile leu thr pro thr pro val asn pro ser thr ala pro ala pro ala pro thr pro thr phe ala gly thr
Reactivity 80%
1.11 (SEQ ID NO:14) gly ala gly val asn val pro ala gly ala gly ala ala ile leu thr pro thr pro val asn pro ser thr ala pro ala pro ala pro NH2
Reactivity 90%
1.12 (SEQ ID NO:15) gly ala gly ala ala ile leu thr pro thr pro val asn pro ser thr ala pro ala pro ala pro thr pro thr phe ala gly thr gln thr pro
Reactivity 80%
1.13 (SEQ ID NO:16) ala tyr lys phe glu gln pro thr leu thr phe gly ala gly val asn val pro ala gly ala gly ala ala ile leu thr pro thr pro val asn pro ser thr ala pro ala pro ala pro
Reactivity 90%
1.14 (SEQ ID NO:17) ala tyr lys phe glu gln pro thr leu thr phe gly ala gly val asn val pro ala gly ala gly ala ala ile leu thr pro thr pro val asn pro ser thr ala pro ala pro ala pro thr pro thr phe ala gly thr gln thr pro
Reactivity 60%
1.15 (SEQ ID NO:18) ala tyr lys phe glu gln pro thr leu thr phe gly ala gly val asn val pro ala gly ala gly ala ala ile leu thr pro thr pro val asn pro ser thr ala pro ala pro ala pro NH$_2$
Reactivity 85%
1.16 (SEQ ID NO:19) gly ala gly val asn val pro ala gly ala gly ala ala ile leu thr pro thr pro val asn pro ser thr ala pro ala pro ala
Reactivity 70%
Peptide No. 2
2.1 (SEQ ID NO:20) asp met asn pro ala asn trp pro arg glu arg ala trp ala leu lys asn pro his leu ala tyr asn pro phe
Reactivity 80%
2.2 (SEQ ID NO:21) asp met asn pro ala asn trp pro arg glu arg ala trp ala leu lys asn pro his leu
Reactivity 75%
2.3 (SEQ ID NO:22) pro ala asn trp pro arg glu arg ala trp ala leu lys asn pro his leu
Reactivity 70%
2.4 (SEQ ID NO:23) pro ala asn trp pro arg glu arg ala trp ala leu lys asn pro his leu ala tyr asn
Reactivity 70%
2.5 (SEQ ID NO:24) trp pro arg glu arg ala trp ala leu lys asn pro his leu ala tyr asn pro phe arg
Reactivity 80%
2.6 (SEQ ID NO:25) glu arg ala trp ala leu lys asn pro his leu ala tyr asn pro phe arg met pro thr thr
Reactivity 70%

2.7 (SEQ ID NO:26) asp met asn pro ala asn trp pro arg glu arg ala trp ala leu

Reactivity 60%

2.8. (SEQ ID NO:27) ala asn trp pro arg glu arg ala trp ala leu lys asn pro his leu ala Reactivity 70%

2.9 (SEQ ID NO:28) asp met asn pro ala asn trp pro arg glu arg ala trp ala leu lys asn pro his leu ala tyr asn pro phe arg met pro thr thr ser thr ala Reactivity 80%

2.10 (SEQ ID NO:29) arg ala trp ala leu lys asn pro his leu ala tyr asn pro phe

Reactivity 80%

Peptide No. 3

3.1 (SEQ ID NO:30) pro arg ala ala val thr gln thr ala ser arg asp ala ala

Reactivity 60%

3.2 (SEQ ID NO:31) ala ser arg asp ala ala asp glu val trp ala leu arg asp gln thr ala Reactivity 80%

TABLE 4

IgM reactivity of the peptide mixture

| Assessment | Reference assay | Peptide assay |
|---|---|---|
| positive | 22 | 21 |
| negative | 13 | 13 |
| false-positive | 0 | 0 |
| false-negative | 0 | 1 |

TABLE 4-continued

IgM reactivity of the peptide mixture

| Assessment | Reference assay | Peptide assay |
|---|---|---|
| Number of IgM sera assayed: | | 35 |
| Sensitivity | : | 95.5% |
| Specificity | : | 100% |

TABLE 5

IgG reactivity of the peptide mixture

| Assessment | Reference assay | Peptide assay |
|---|---|---|
| positive | 133 | 132 |
| negative | 152 | 149 |
| false-positive | 0 | 3 |
| false-negative | 0 | 1 |
| Number of IgG sera assayed: | | 285 |
| Sensitivity | : | 99.25% |
| Specificity | : | 98.03% |

We claim:

1. A peptide which reacts specifically with antibodies against HCMV,
wherein said peptide consists of at least one amino-acid sequence selected from the group consisting of
$AS_e$-gly ala gly ala ala ile leu-$BS_m$ (peptide 1) (SEQ ID NO.: 1),
$CS_n$-arg ala trp ala leu-$Ds_o$ (peptide 2) (SEQ ID NO.:2), and
$ES_p$-ala ser arg asp ala ala-$Fs_q$ (peptide 3) (SEQ ID NO.:3) where AS, BS, CS, DS, ES and FS are, independently of one another, any appropriate amino acid and
    e is an integer from 0 to 14, and m is an integer from 0 to 7, or e is an integer from 0 to 2 and m is an integer from 0 to 19,
    n and o are, independently of one another, integers from 0 to 18, and
    p and q are, independently of one another, integers from 0 to 11,
wherein said peptide reacts specifically with antibodies against HCMV.

2. A peptide as claimed in claim 1, which contains at least one of the following amino-acid sequences:
for peptide 1:
    residues 6–26 of peptide 1.1 (SEQ ID NO. 4) corresponding to Gln Pro Thr Leu Thr Phe Gly Ala Gly Val Asn Val Pro Ala Gly Ala Gly Ala Ala lle Leu,
    residues 3–28 of peptide 1.2 (SEQ ID NO. 5) corresponding to Gln Pro Thr Leu Thr Phe Gly Ala Gly Val Asn Val Pro Ala Gly Ala Gly Ala Ala lle Leu Thr Pro Thr Pro Val,
    residues 15–28 of peptide 1.2 (SEQ ID NO. 5) corresponding to Pro Ala Gly Ala Gly Ala Ala lle Leu Thr Pro Thr Pro Val,
    residues 15–33 of peptide 1.3 (SEQ ID NO. 6) corresponding to Gln Pro Thr Leu Thr Phe Gly Ala Gly Val Asn Val Pro Ala Gly Ala Gly Ala Ala lle Leu Thr Pro Thr Pro Val Asn Pro Ser Thr Ala,
    residues 16–38 of peptide 1.4 (SEQ ID NO. 7) corresponding to Pro Ala Gly Ala Gly Ala Ala lle Leu Thr Pro Thr Pro Val Asn Pro Ser Thr Ala Pro Ala Pro Ala,
    residues 12–34 of peptide 1.5 (SEQ ID NO. 8) corresponding to Pro Ala Gly Ala Gly Ala Ala lle Leu Thr Pro Thr Pro Val Asn Pro Ser Thr Ala Pro Ala Pro Ala,
    residues 1–27 of peptide 1.5 (SEQ ID NO. 8) corresponding to Pro Thr Leu Thr Phe Gly Ala Gly Val Asn Val Pro Ala Gly Ala Gly Ala Ala lle Leu Thr Pro Thr Pro Val Asn Pro,
    residues 12–35 of peptide 1.6 (SEQ ID NO. 9) corresponding to Pro Ala Gly Ala Gly Ala Ala lle Leu Thr Pro Thr Pro Val Asn Pro Ser Thr Ala Pro Ala Pro Ala Pro $NH_2$,
    1.7 (SEQ ID NO. 10) Val Asn Val Pro Ala Gly Ala Gly Ala Ala lle Leu Thr Pro Thr Pro Val Asn Pro,
    residues 4–19 of peptide 1.7 (SEQ ID NO. 10) corresponding to Pro Ala Gly Ala Gly Ala Ala lle Leu Thr Pro Thr Pro Val Asn Pro,
    1.8 (SEQ ID NO. 11) Pro Ala Gly Ala Gly Ala Ala lle Leu Thr Pro Thr Pro Val Asn Pro Ser Thr Ala Pro Ala,
    residues 1–19 of peptide 1.9 (SEQ ID NO. 12) corresponding to Val Asn Val Pro Ala Gly Ala Gly Ala Ala lle Leu Thr Pro Thr Pro Val Asn Pro,
    residues 4–31 of peptide 1.9 (SEQ ID NO. 12) corresponding to Pro Ala Gly Ala Gly Ala Ala lle Leu Thr Pro Thr Pro Val Asn Pro Ser Thr Ala Pro Ala Pro Ala Pro Thr Pro Thr Phe,
    residues 1–28 of peptide 1.10 (SEQ ID NO. 13) corresponding to Pro Ala Gly Ala Gly Ala Ala lle Leu Thr Pro Thr Pro Val Asn Pro Ser Thr Ala Pro Ala Pro Ala Pro Thr Pro Thr Phe,
    residues 7–30 of peptide 1.11 (SEQ ID NO. 14) corresponding to Pro Ala Gly Ala Gly Ala Ala lle Leu Thr Pro Thr Pro Val Asn Pro Ser Thr Ala Pro Ala Pro Ala Pro $NH_2$,
    residues 1–22 of peptide 1.11 (SEQ ID NO. 14) corresponding to Gly Ala Gly Val Asn Val Pro Ala Gly Ala Gly Ala Ala lle Leu Thr Pro Thr Pro Val Asn Pro $NH_2$,
    residues 1–26 of peptide 1.12 (SEQ ID NO. 15) corresponding to Gly Ala Gly Ala Ala lle Leu Thr Pro Thr Pro Val Asn Pro Ser Thr Ala Pro Ala Pro Ala Pro Thr Pro Thr Phe,
    residues 1–28 of peptide 1.13 (SEQ ID NO. 16) corresponding to Gln Pro Thr Leu Thr Phe Gly Ala Gly Val Asn Val Pro Ala Gly Ala Gly Ala Ala lle Leu Thr Pro Thr Pro Val Asn Pro
    residues 18–45 of peptide 1.14 (SEQ ID NO. 17) corresponding to Pro Ala Gly Ala Gly Ala Ala lle Leu Thr Pro Thr Pro Val Asn Pro Ser Thr Ala Pro Ala Pro Ala Pro Thr Pro Thr Phe,
    residues 7–29 of peptide 1.16 (SEQ ID NO. 19) corresponding to Pro Ala Gly Ala Gly Ala Ala lle Leu Thr Pro Thr Pro Val Asn Pro Ser Thr Ala Pro Ala Pro Ala,
    residues 1–22 of peptide 1.16 (SEQ ID NO. 19) corresponding to Gly Ala Gly Val Asn Val Pro Ala Gly Ala Gly Ala Ala lle Leu Thr Pro Thr Pro Val Asn Pro.

3. A peptide mixture which contains at least two peptides selected from the group consisting of peptides 1, 2 and 3 as claimed in claim 1.

4. A peptide as claimed in claim 1, comprising residues 6–26 of peptide 1.1 (SEQ ID NO. 4) corresponding to:
    Gln Pro Thr Leu Thr Phe Gly Ala Gly Val Asn Val Pro Ala Gly Ala Gly Ala Ala lle Leu.

5. A peptide as claimed in claim 1, comprising residues 3–28 of peptide 1.2 (SEQ ID NO. 5) corresponding to:
Gln Pro Thr Leu Thr Phe Gly Ala Gly Val Asn Val Pro Ala Gly Ala Gly Ala Ala lle Leu Thr Pro Thr Pro Val.

6. A peptide as claimed in claim 1, comprising residues 15–33 of peptide 1.3 (SEQ ID NO. 6) corresponding to:
Gln Pro Thr Leu Thr Phe Gly Ala Gly Val Asn Val Pro Ala Gly Ala Gly Ala Ala lle Leu Thr Pro Thr Pro Val Asn Pro Ser Thr Ala.

7. A peptide as claimed in claim 1, comprising residues 16–38 of peptide 1.4 (SEQ ID NO. 7) corresponding to:
Pro Ala Gly Ala Gly Ala Ala lle Leu Thr Pro Thr Pro Val Asn Pro Ser Thr Ala Pro Ala Pro Ala.

8. A peptide as claimed in claim 1, comprising residues 1–28 of sequence 1.5 (SEQ ID NO: 8) corresponding to:
Pro Thr Leu Thr Phe Gly Ala Gly Val Asn Val Pro Ala Gly Ala Gly Ala Ala lle Leu Thr Pro Thr Pro Val Asn Pro Ser.

9. A peptide as claimed in claim 1, comprising the residues 1–28 of sequence 1.6 (SEQ ID NO. 9) corresponding to:
Pro Thr Leu Thr Phe Gly Ala Gly Val Asn Val Pro Ala Gly Ala Gly Ala Ala lle Leu Thr Pro Thr Pro Val Asn Pro Ser $NH_2$.

10. A peptide as claimed in claim 1, comprising the sequence 1.7 (SEQ ID NO. 10):
Val Asn Val Pro Ala Gly Ala Gly Ala Ala lle Leu Thr Pro Thr Pro Val Asn Pro.

11. A peptide as claimed in claim 1, comprising the sequence 1.8 (SEQ ID NO: 11):
Pro Ala Gly Ala Gly Ala Ala lle Leu Thr Pro Thr Pro Val Asn Pro Ser Thr Ala Pro Ala.

12. A peptide as claimed in claim 1, comprising the residues 1–20 of sequence 1.9 (SEQ ID NO. 12) corresponding to:
Val Asn Val Pro Ala Gly Ala Gly Ala Ala lle Leu Thr Pro Thr Pro Val Asn Pro Ser.

13. A peptide as claimed in claim 1, comprising the residues 1–28 of sequence 1.10 (SEQ ID NO. 13) corresponding to:
Pro Ala Gly Ala Gly Ala Ala lle Leu Thr Pro Thr Pro Val Asn Pro Ser Thr Ala Pro Ala Pro Ala Pro Thr Pro Thr Phe.

14. A peptide as claimed in claim 1, comprising the residues 7–30 of sequence 1.11 (SEQ ID NO. 14) corresponding to:
Pro Ala Gly Ala Gly Ala Ala lle Leu Thr Pro Thr Pro Val Asn Pro Ser Thr Ala Pro Ala Pro Ala Pro $NH_2$.

15. A peptide as claimed in claim 1, comprising residues 1–26 of peptide 1.12 (SEQ ID NO. 15) corresponding to:
Gly Ala Gly Ala Ala lle Leu Thr Pro Thr Pro Val Asn Pro Ser Thr Ala Pro Ala Pro Ala Pro Thr Pro Thr Phe.

16. A peptide as claimed in claim 1, comprising residues 6–36 of peptide 1.13 (SEQ ID NO. 16) corresponding to:
Gln Pro Thr Leu Thr Phe Gly Ala Gly Val Asn Val Pro Ala Gly Ala Gly Ala Ala lle Leu Thr Pro Thr Pro Val Asn Pro.

17. A peptide as claimed in claim 1, comprising residues 18–45 of peptide 1.14 (SEQ ID NO. 17) corresponding to:
Pro Ala Gly Ala Gly Ala Ala lle Leu Thr Pro Thr Pro Val Asn Pro Ser Thr Ala Pro Ala Pro Ala Pro Thr Pro Thr Phe.

18. A peptide as claimed in claim 1, comprising the sequence 1.16 (SEQ ID NO. 19):
Gly Ala Gly Val Asn Val Pro Ala Gly Ala Gly Ala Ala lle Leu Thr Pro Thr Pro Val Asn Pro Ser Thr Ala Pro Ala Pro Ala.

19. A peptide as claimed in claim 1, comprising the sequence 2.1 (SEQ ID NO.20):
Asp Met Asn Pro Ala Asn Trp Pro Arg Glu Arg Ala Trp Ala Leu Lys Asn Pro His Leu Ala Tyr Asn Pro Phe.

20. A peptide as claimed in claim 1, comprising the sequence 2.2 (SEQ ID NO.22):
Asp Met Asn Pro Ala Asn Trp Pro Arg Glu Arg Ala Trp Ala Leu Lys Asn Pro His Leu.

21. A peptide as claimed in claim 1, comprising the sequence 2.3 (SEQ ID NO. 22):
Pro Ala Asn Trp Pro Arg Glu Arg Ala Trp Ala Leu Lys Asn Pro His Leu.

22. A peptide as claimed in claim 1, comprising the sequence 2.4 (SEQ ID NO.23):
Pro Ala Asn Trp Pro Arg Glu Arg Ala Trp Ala Leu Lys Asn Pro His Leu Ala Tyr Asn.

23. A peptide as claimed in claim 1, comprising the sequence 2.5 (SEQ ID NO.24):
Trp Pro Arg Glu Arg Ala Trp Ala Leu Lys Asn Pro His Leu Ala Tyr Asn Pro Phe Arg.

24. A peptide as claimed in claim 1, comprising the sequence 2.6 (SEQ ID NO. 25):
Glu Arg Ala Trp Ala Leu Lys Asn Pro His Leu Ala Tyr Asn Pro Phe Arg Met Pro Thr Thr.

25. A peptide as claimed in claim 1, comprising the sequence 2.7 (SEQ ID NO.26):
Asp Met Asn Pro Ala Asn Trp Pro Arg Glu Arg Ala Trp Ala Leu.

26. A peptide as claimed in claim 1, comprising the sequence 2.8 (SEQ ID NO. 27):
Ala Asn Trp Pro Arg Glu Arg Ala Trp Ala Leu Lys Asn Pro His Leu Ala.

27. A peptide as claimed in claim 1, comprising the sequence 2.9 (SEQ ID NO. 28):
Asp Met Asn Pro Ala Asn Trp Pro Arg Glu Arg Ala Trp Ala Leu Lys Asn Pro His Leu Ala Tyr Asn Pro Phe Arg Met Pro Thr Thr Ser Thr Ala.

28. A peptide as claimed in claim 1, comprising the sequence 2.10 (SEQ ID NO. 29):
Arg Ala Trp Ala Leu Lys Asn Pro His Leu Ala Tyr Asn Pro Phe.

29. A peptide as claimed in claim 1, which contains at least one of the following amino-acid sequences:
2.1 (SEQ ID NO. 20)
Asp Met Asn Pro Ala Asn Trp Pro Arg Glu Arg Ala Trp Ala Leu Lys Asn Pro His Leu Ala Tyr Asn Pro Phe
2.2 (SEQ ID NO. 21)
Asp Met Asn Pro Ala Asn Trp Pro Arg Glu Arg Ala Trp Ala Leu Lys Asn Pro His Leu
2.3 (SEQ ID NO. 22)
Pro Ala Asn Trp Pro Arg Glu Arg Ala Trp Ala Leu Lys Asn Pro His Leu
2.4 (SEQ ID NO. 23)
Pro Ala Asn Trp Pro Arg Glu Arg Ala Trp Ala Leu Lys Asn Pro His Leu Ala Tyr Asn
2.5 (SEQ ID NO. 24)
Trp Pro Arg Glu Arg Ala Trp Ala Leu Lys Asn Pro His Leu Ala Tyr Asn Pro Phe Arg
2.6 (SEQ ID NO. 25)
Glu Arg Ala Trp Ala Leu Lys Asn Pro His Leu Ala Tyr Asn Pro Phe Arg Met Pro Thr Thr
2.7 (SEQ ID NO. 26)
Asp Met Asn Pro Ala Asn Trp Pro Arg Glu Arg Ala Trp Ala Leu 2.8 (SEQ ID NO. 27)
   Ala Asn Trp Pro Arg Glu Arg Ala Trp Ala Leu Lys Asn Pro His Leu Ala
2.9 (SEQ ID NO. 28)
   Asp Met Asn Pro Ala Asn Trp Pro Arg Glu Arg Ala Trp Ala Leu Lys Asn Pro His Leu Ala Tyr Asn Pro Phe Arg Met Pro Thr Thr Ser Thr Ala
2.10 (SEQ ID NO. 29)
   Arg Ala Trp Ala Leu Lys Asn Pro His Leu Ala Tyr Asn Pro Phe.

30. A peptide as claimed in claim 1, comprising the sequence 3.1 (SEQ ID NO. 30) Pro Arg Ala Ala Val Thr Gln Thr Ala Ser Arg Asp Ala Ala.

31. A peptide as claimed in claim 1, comprising the sequence 3.2 (SEQ ID NO. 31) Ala Ser Arg Asp Ala Ala Asp Glu Val Trp Ala Leu Arg Asp Gln Thr Ala.

32. A peptide as claimed in claim 1, which contains at least one of the following amino-acid sequences:
   3.1 (SEQ ID NO. 30)
      Pro Arg Ala Ala Val Thr Gln Thr Ala Ser Arg Asp Ala Ala
   3.2 (SEQ ID NO. 31)
      Ala Ser Arg Asp Ala Ala Asp Glu Val Trp Ala Leu Arg Asp Gln Thr Ala.

33. A peptide consisting of a peptide as claimed in claim 1, whose amino-acid sequence is modified by replacement of one or more amino acids with structurally related amino acids, by deletion of one or more amino acids, or by acid amidation, wherein the immunoreactivity of the peptide is not directly altered or is improved.

34. A peptide as claimed in claim 1, wherein the peptide has been synthesized chemically.

35. A peptide as claimed in claim 1, comprising residues 15–28 of peptide 1.2 (SEQ ID NO. 5) corresponding to:
   Pro Ala Gly Ala Gly Ala Ala Ile Leu.

36. A peptide as claimed in claim 1, comprising residues 12–34 of sequence 1.5 (SEQ ID NO. 8) corresponding to:
   Pro Ala Gly Ala Gly Ala Ala Ile Leu Thr Pro Thr Pro Val Asn Pro Ser Thr Ala Pro Ala Pro Ala.

37. A peptide as claimed in claim 1, comprising residues 12–35 of sequence 1.6 (SEQ ID NO. 9) corresponding to:
   Pro Ala Gly Ala Gly Ala Ala Ile Leu Thr Pro Thr Pro Val Asn Pro Ser Thr Ala Pro Ala Pro Ala Pro.

38. A peptide as claimed in claim 1, comprising residues 4–19 of sequence 1.7 (SEQ ID NO: 10) corresponding to:
   Pro Ala Gly Ala Gly Ala Ala Ile Leu Thr Pro Thr Pro Val Asn Pro.

39. A peptide as claimed in claim 1, comprising the residues 7–31 of sequence 1.9 (SEQ ID NO: 12) corresponding to:
   Pro Ala Gly Ala Gly Ala Ala Ile Leu Thr Pro Thr Pro Val Asn Pro Ser Thr Ala Pro Ala Pro Ala Pro Thr Pro Thr Phe.

40. A peptide as claimed in claim 1, comprising the residues 1–22 of sequence 1.11 (SEQ ID NO: 14) corresponding to:
   Gly Ala Gly Val Asn Val Pro Ala Gly Ala Gly Ala Ala Ile Leu Thr Pro Thr Pro Val Asn Pro.

41. A recombinant fusion protein comprising the peptide of claim 1.

42. A peptide consisting of the peptide of claim 1 and an extension of 1 to 40 amino acids, wherein the extension does not comprise contiguous pp150 amino acid sequence.

43. The peptide of claim 1 covalently bound to a solid support or carrier.

44. A marker selected from the group consisting of radioactive isotopes, fluorescent compounds, chromogenic compounds, chemiluminescent compounds, chemiluminogenic compounds, and enzymes bound to the peptide of claim 1.

45. A peptide consisting of a peptide as claimed in claim 2, whose amino-acid sequence is modified by replacement of one or more amino acids with structurally related amino acids, by deletion of one or more amino acids, or by acid amidation, wherein the immunoreactivity of the peptide is either not directly altered or is improved.

46. A peptide as claimed in claim 2, wherein the peptide has been synthesized chemically.

47. A peptide as claimed in claim 45, wherein modification of the amino-acid sequence is performed by thioglycolic acid amidation or carboxy-terminal amidation.

48. A peptide as claimed in claim 45, wherein modification by carboxy-terminal amidation is performed by ammonia or methylamine.

49. The peptide mixture as claimed in claim 3, wherein the peptides are linked together directly or via a spacer.

50. A peptide consisting of a peptide as claimed in claim 29, whose amino-acid sequence is modified by replacement of one or more amino acids with structurally related amino acids, by deletion of one or more amino acids, or by acid amidation, wherein the immunoreactivity of the peptide is not directly altered or is improved.

51. A peptide as claimed in claim 29, wherein the peptide has been synthesized chemically.

52. A peptide consisting of a peptide as claimed in claim 32, whose amino-acid sequence is modified by replacement of one or more amino acids with structurally related amino acids, by deletion of one or more amino acids, or by acid amidation, wherein the immunoreactivity of the peptide is not directly altered or is improved.

53. A peptide as claimed in claim 32, wherein the peptide has been synthesized chemically.

54. A peptide as claimed in claim 33, wherein modification of the amino-acid sequence is performed by thioglycolic acid amidation or carboxy-terminal amidation.

55. A peptide as claimed in claim 33, wherein modification by carboxy-terminal amidation is performed by ammonia or methylamine.

56. A peptide as claimed in claim 50, wherein modification of the amino-acid sequence is performed by thioglycolic acid amidation or carboxy-terminal amidation.

57. A peptide as claimed in claim 50, wherein modification by carboxy-terminal amidation is performed by ammonia or methylamine.

58. A peptide as claimed in claim 52, wherein modification of the amino-acid sequence is performed by thioglycolic acid amidation or carboxy-terminal amidation.

59. A peptide as claimed in claim 52, wherein modification by carboxy-terminal amidation is performed by ammonia or methylamine.

60. The recombinant fusion protein of claim 41 wherein the fusion protein contains a portion of β-galactosidase.

61. The peptide of claim 42 wherein the extension is selected from the group consisting of cysteine, and about 2 to 20 hydrophobic amino acids.

62. The peptide of claim 43, wherein the carrier is a carrier protein or polylysine.

* * * * *